(12) United States Patent
Lamontagne et al.

(10) Patent No.: US 9,052,272 B2
(45) Date of Patent: Jun. 9, 2015

(54) DEVICE FOR ANALISING A RADIATING MATERIAL USING A MICROPROBE

(71) Applicant: COMMISSARIAT A L'ENERGIE ATOMIQUE ET AUX ENERGIES ALTERNATIVES, Paris (FR)

(72) Inventors: Jérôme Lamontagne, Manosque (FR); Thierry Blay, Jouques (FR); Philippe Benard, Eaubonne (FR)

(73) Assignee: Commisariat a L'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 14/356,332

(22) PCT Filed: Nov. 15, 2012

(86) PCT No.: PCT/FR2012/000462
§ 371 (c)(1),
(2) Date: May 5, 2014

(87) PCT Pub. No.: WO2013/072580
PCT Pub. Date: May 23, 2013

(65) Prior Publication Data
US 2014/0326880 A1 Nov. 6, 2014

(30) Foreign Application Priority Data
Nov. 15, 2011 (FR) ..................... 11 03461

(51) Int. Cl.
*G01Q 10/04* (2010.01)
*G01N 23/22* (2006.01)
*H01J 37/18* (2006.01)
*H01J 37/252* (2006.01)
*G01N 23/225* (2006.01)

(52) U.S. Cl.
CPC .......... *G01N 23/2204* (2013.01); *H01J 37/185* (2013.01); *H01J 37/252* (2013.01); *H01J 2237/184* (2013.01); *H01J 2237/204* (2013.01); *G01N 23/2252* (2013.01)

(58) Field of Classification Search
CPC ....... G01Q 10/00; G01Q 10/02; G01Q 10/04; G01Q 10/045; G01Q 10/06; G01Q 10/065; G01Q 20/00; G01Q 20/02; G01Q 20/04
USPC ............... 250/440.11, 441.11, 442.11, 443.1; 850/1, 2, 3, 4, 5, 6, 7
See application file for complete search history.

(56) References Cited

U.S. PATENT DOCUMENTS

| 4,033,904 A * | 7/1977 | Gerlach et al. ........... 250/440.11 |
| 2005/0139781 A1 | 6/2005 | Hazaki et al. |
| 2011/0093991 A1* | 4/2011 | Gunji et al. ..................... 850/53 |

FOREIGN PATENT DOCUMENTS

| EP | 0 562 874 A1 | 9/1993 |
| JP | 2001-153760 A | 6/2001 |
| JP | 2005-203556 A | 6/2005 |

OTHER PUBLICATIONS

Machine English Language Translation & Abstract of 2001-153760 A.
Machine English Language Translation & Abstract of 2005-203556 A.

* cited by examiner

*Primary Examiner* — Nicole Ippolito
(74) *Attorney, Agent, or Firm* — Ladas & Parry LLP (57) ABSTRACT

The invention relates to an analysis device comprising a main enclosure fitted with a secondary enclosure, a microprobe placed inside the main enclosure and fitted with an airlock and with a motion object, and a movable sample support that is movable from the secondary enclosure to the airlock and from the airlock to the motion object. Each of the airlock and the motion object includes a respective guide member for guiding the movable sample support and a respective sensor for detecting the presence of the movable sample support.

16 Claims, 7 Drawing Sheets

DEVICE FOR ANALISING A RADIATING MATERIAL USING A MICROPROBE

RELATED APPLICATION INFORMATION

This application is a 371 of International Application PCT/FR2012/000462 filed 15 Nov. 2012 entitled "Device For Analysing A Radiating Material Using A Microprobe", which was published on 23 May 2013, with International Publication Number WO WO2013/072580 A1 and which claims priority from French Patent Application 1103461, filed 15 Nov. 2011, the content of which is incorporated herein by reference.

TECHNICAL FIELD

The present invention relates to a device for analyzing a radiating material with the help of a microprobe.

The invention applies in particular to analyzing a sample extracted from a nuclear fuel pellet.

PRIOR ART

It is known to analyze the chemical composition of a sample by analyzing the X-rays, and in particular the X-ray spectrum, emitted by a zone of the sample when. subjected to bombardment. Depending on whether the sample is subjected to electron bombardment or to ion bombardment, the apparatus used for performing the analysis may be referred to as an electron microprobe or an ion microprobe.

To this end, an electron microprobe comprises in particular an analysis chamber for receiving the sample, an electron gun for emitting an electron beam, an electron column for focusing the electron beam on the sample placed in the analysis chamber, and spectrometers arranged to receive the X-rays emitted by the sample during interaction between the electrons and the material of the sample.

In order to be able to analyze all or part of a sample, the sample is generally placed on an XYZ-table serving to move the point-line analysis zone that is subjected to electron bombardment along two orthogonal axes of a plane perpendicular to the axis of the electron beam and also along that axis. This XYZ-table (movable along three orthogonal axes) that supports the sample for analysis is generally referred to as a "motion object".

The apparatus may also include an airlock connected to the analysis chamber and in which it is possible to establish a partial vacuum, in order to enable a sample that has been placed in the airlock to be inserted into the analysis chamber without completely "breaking" the vacuum in the analysis chamber.

In order to analyze radioactive samples with such apparatus, it is possible to envisage placing the apparatus in a shielded cell fitted with a glove box that is used for manipulating or remotely manipulating the samples before they are inserted into the analysis apparatus and after they have been extracted from the apparatus. The term "remote manipulation" is used to cover the action of manipulating from a distance, using means that are known to the person skilled in the art, for example manual or electrical grippers.

Known devices for analyzing a radiating material with the help of a microprobe do not make it possible to guarantee a sufficient level of safety.

It is necessary to avoid any rupture in the confinement of the sample from the glove box to the analysis chamber so as to avoid contaminating the shielded cell with radioactive dust coming from the sample.

It is also necessary to be able to transfer the sample from the glove box to the motion object and to transfer it in the opposite direction, even in the event of a failure of the analysis apparatus, and it is necessary to be able to monitor such transfers reliably.

Another problem to be solved is to avoid transmitting mechanical vibration to the analysis apparatus as a result of the forced ventilation that serves to keep the pressure inside the glove box below the pressure inside the shielded cell.

SUMMARY OF THE INVENTION

An object of the invention is to propose a device for analyzing a material with the help of a microprobe, which device is improved and/or remedies, at least in part, the shortcomings or drawbacks of known devices for performing microprobe analysis.

In an aspect of the invention, there is provided an analysis device that comprises a main enclosure such as a shielded cell that is fitted with a secondary enclosure such as a glove box, together with a microprobe placed inside the main enclosure and fitted with an airlock; the device also comprises a movable sample support that is movable from the secondary enclosure to the airlock and from the airlock to the motion object; furthermore, each of the airlock and the motion object includes a respective guide member for guiding the movable sample support while it is being moved, together with respective means for detecting the presence of the movable sample support in order to monitor the position of the movable support.

The motion object may also include a (mechanical) abutment serving to hold the movable sample support in an analysis position.

The analysis device preferably further includes a slidable control bar, such as a rod, for moving the movable sample support from the airlock to the motion object and back again.

Under such circumstances, the movable sample support and the sliding control bar may have respective complementary mechanical coupling members designed for engaging mutually so as to provide a mechanical connection between the control bar and the movable sample support.

The analysis device then preferably includes locking means that allow the coupling members to be mutually separated in the analysis position of the movable sample support on the motion object, and also in a transfer position for the movable sample support inside the airlock, and that prevents such separation in all positions of the movable sample support that are intermediate between the analysis position and the transfer position.

In a preferred embodiment, the analysis device also includes alignment means that, serve for aligning the guide member or the airlock and the guide member of the motion object in the event of a power supply failure to the drive motors driving the XYZ-table in order to make it possible under such circumstances to return the movable sample support from the motion object to the airlock.

For each axis of the XYZ-table, these "manual" alignment means may comprise a drive member, such as a drive wheel engaging a wormscrew, for driving the table to move along that axis; the drive member being suitable for being actuated by a manipulator member passing through a wall of the main enclosure.

For each axis of the XYZ-table, these alignment means preferably also include, a respective position sensor sensitive to the position of the table along that axis, and a display device connected to the sensor in order to display in a manner that is visible from outside the main enclosure the position of the table along that axis, thereby enabling an operator acting on the manipulator member to control the movement of the XYZ-table manually along each of these axes so as to obtain mutual alignment of the respective guide members incorporated in the motion object and in the airlock.

Each guide member may comprise a rail segment on or against which the movable sample support can slip, slide, or roll.

For this purpose, the movable sample support may be fitted with skids and/or wheels to facilitate its movement on or along the guide member.

Each means for detecting the presence of the movable sample support may comprise an electromechanical sensor or an electromagnetic sensor.

In an embodiment, a wall of the airlock is transparent so as to make it possible to monitor visually the presence of the movable sample support inside the airlock.

In order to monitor the position of the sample, and also the position of the movable sample support, a visible mark may also be provided on the movable sample support so as to facilitate visual monitoring of the presence of the movable support inside the analysis chamber by means of an optical microscope incorporated in the analysis apparatus.

In this embodiment, the analysis device also includes a hollow structure connecting the airlock to the secondary enclosure, within which the movable sample support can move so as to enable the movable sample support to be transferred from the secondary enclosure to the airlock, and back again.

This hollow structure comprises a dustproof covering to avoid the main enclosure being contaminated by radioactive dust coming from the sample carried by the movable support.

In addition, this hollow structure, and preferably said dustproof covering, presents mechanical stiffness that is sufficiently low to greatly limit (or eliminate) any transmission of vibration from the secondary enclosure to the airlock, and thus to the analysis apparatus.

In an embodiment, the hollow structure is essentially constituted by a corrugated tubular covering made of a plastics material, in particular a covering in the form of a bellows.

Other aspects, characteristics, and advantages of the invention appear from the following description made with reference to the accompanying figures showing preferred embodiments of the invention without any limiting character.

BRIEF DESCRIPTION OF THE FIGURES

the configuration shown in FIG. 2 corresponds to a step of loading a sample for analysis on a movable sample support in the glove box; this configuration may also correspond to a step of unloading a sample that has already been analyzed.

the configuration shown in FIG. 3 corresponds to a step of closing the airlock containing the movable sample support so as to evacuate the airlock before transferring the sample support into the analysis chamber; this configuration may also correspond to a step of repressurizing the airlock containing a movable support carrying a sample that has been analyzed.

the configuration shown in FIG. 4 corresponds to a step of transferring the movable sample support inside the analysis chamber by means of a sliding control rod, prior to removing the rod and isolating the analysis chamber; this configuration may also correspond to a step of using the control rod to recover a movable support carrying a sample that has been analyzed; and the configuration shown in FIG. 5 corresponds to a step of analyzing the sample carried by the movable sample support.

DETAILED DESCRIPTION OF THE INVENTION

Unless specified explicitly or implicitly to the contrary, elements or members that are structurally or functionally identical or similar are given identical references in the various figures.

Figure 1:
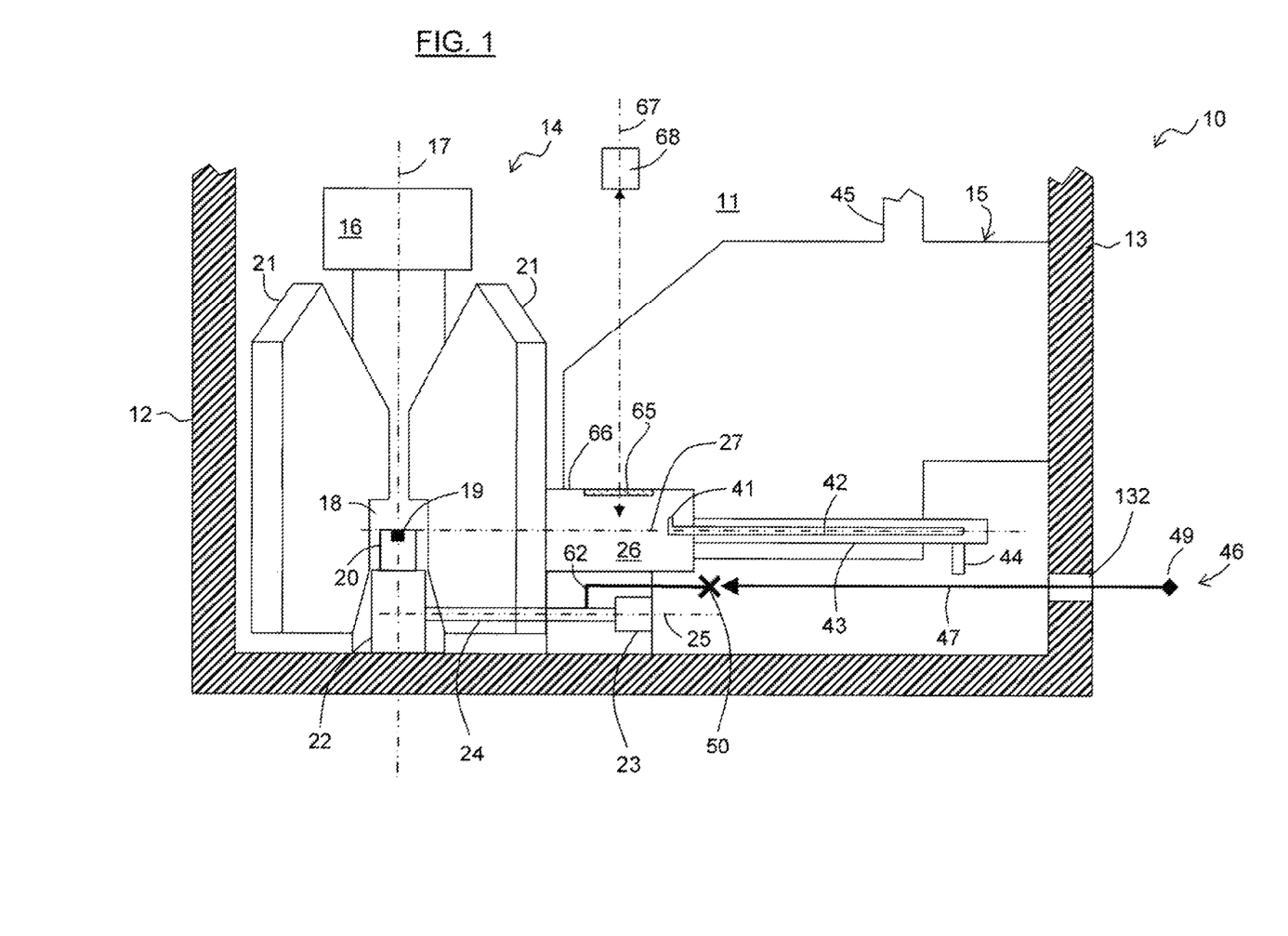
FIG. 1 is a diagrammatic side view of a device for analyzing samples of radiating materials.

With reference to FIG. 1 in particular, the analysis device 10 comprises a main enclosure or "cell" 11 that is defined by shielded walls 12, 13.

The cell 11 contains a microprobe 14 and a glove box 15.

The glove box or "secondary enclosure" is connected by two ducts, such as the duct 45, both to an extractor and to a blower fan (not shown), such that the volume defined by the glove box is maintained at a pressure lower than that of the cell so as to avoid the cell being contaminated by radioactive gas or dust present in the glove box.

The microprobe 14 comprises an electron gun 16 producing a beam of electrons directed along a vertical axis 17 in an electron column towards an analysis chamber 18 that receives a sample 19 for analysis.

For this purpose, the sample 19 is placed on a support 20 inside the chamber 18 in a position such that a portion of the sample is arranged on the axis 17.

The microprobe 14 has a plurality of spectrometers 21 arranged around the chamber 18 to receive the X-rays emitted by the sample when subjected to the electron beam.

In order to be able to analyze an extensive zone of the sample, the sample is movable inside the chamber 18 along the axis 17 and along two orthogonal axes of a plane perpendicular to the axis 17.

For this purpose, the support 20 carrying the sample is mounted on table 22 that is movable along these three orthogonal axes in pairs.

The movement of the table 22, and consequently the movement of the support 20 and of the sample 19 along each of these three axes, is obtained by actuating a rotary electric motor 23 that drives a wormscrew 24 extending along a horizontal axis 25 so that the screw rotates about the axis 25.

In known manner, a nut (not shown) connected to the table and engaged with the screw 24 causes the table to move under the effect. of the screw being turned.

In order to avoid detracting from the clarity of FIG. 1, only one of the three drive systems 23, 24 for driving the motion object 22 is shown in this figure.

The microprobe 14 is fitted with an airlock 26 enabling a sample to be inserted in the analysis chamber, and subsequently to be extracted from the chamber after it has been analyzed, along a horizontal axis 27.

Figure 6:
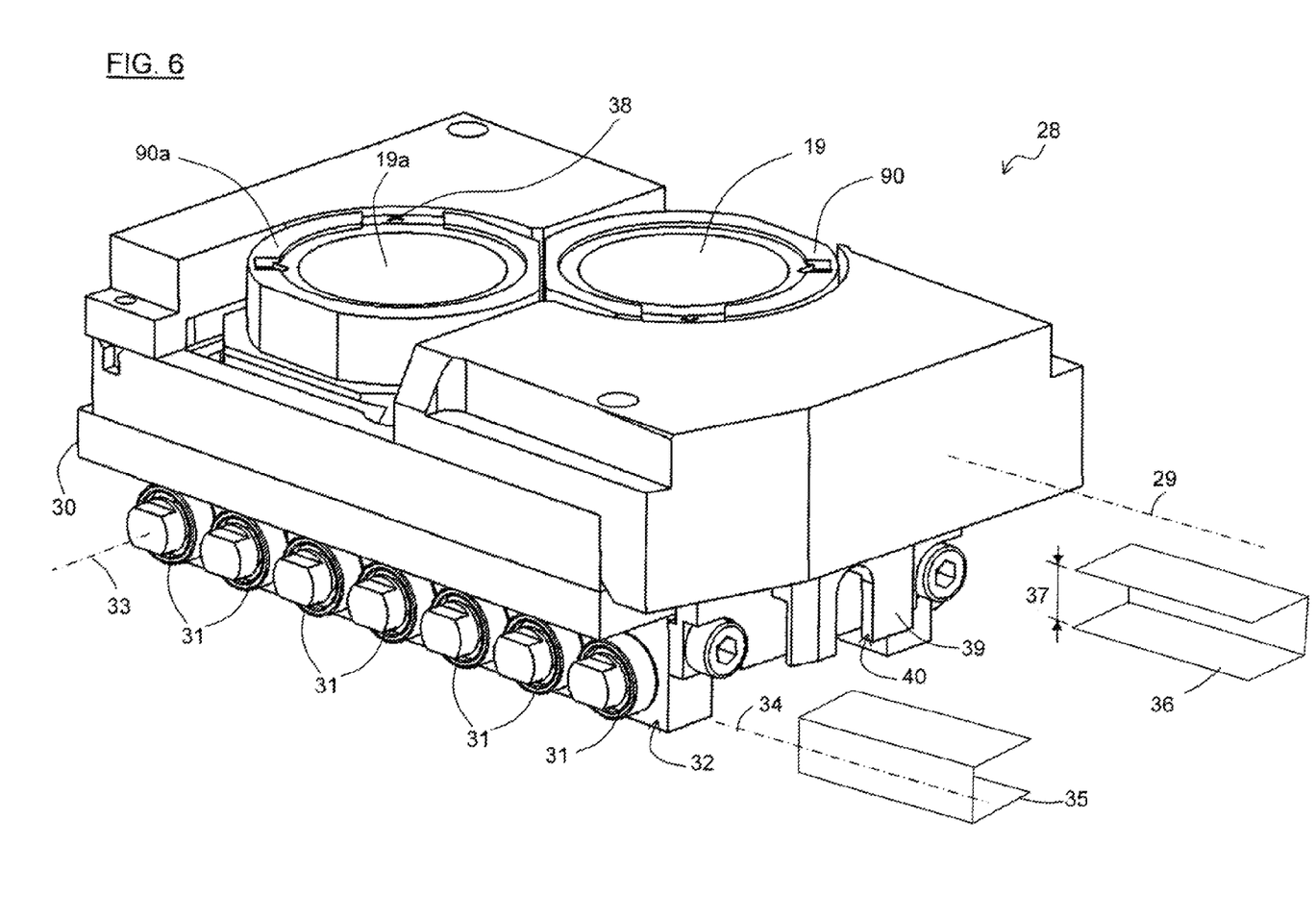
FIG. 6 is a diagrammatic perspective view of a movable sample support.

For its movement inside the analysis device 10, the sample 19 is placed on a movable support or "vehicle" 28 such as that shown in FIG. 6.

With reference to FIG. 6 in particular, the vehicle 28 is of elongate shape along a longitudinal axis 29.

The vehicle 28 comprises a frame 30 having a bottom portion that is fitted on each of its two longitudinal lateral faces 32 (only one of which is visible in FIG. 6) with seven wheels 31 mounted to rotate freely about transverse axes such as the axis referenced 33.

These wheels are in alignment along an axis 34 parallel to the axis 29 so that they can be inserted in a segment of guide rail such as the segments referenced 35 and 36 in FIG. 6.

Each of these rails is of channel-section, comprising three substantially plane longitudinal strips that are orthogonal in pairs.

The height 37 between the two parallel horizontal strips of each rail 35, 36 is matched to the diameter of the wheels 31 of the vehicle 28 so that the vehicle 28 can run on the respective horizontal bottom strips of the rails 35 and 36.

In its top portion, the vehicle 28 receives two sample-carrier cups 90 and 90a in which two samples 19 and 19a are placed respectively, the samples being in the form of pellets or disks: a sample 19 for analysis and a sample 19a of known nature and composition for acting as a reference when analyzing the sample 19 by spectral analysis of the X-rays emitted by the sample.

The top face of at least one of the cups 90, 90a carries a visible mark 38 that can be seen by an operator using an optical microscope (not shown) forming part of the microprobe, when the vehicle 28 is correctly positioned in the analysis position inside the analysis chamber on the motion object 20, 22.

At one of its two longitudinal ends, the vehicle 28 carries a plate 39 extending perpendicularly to the axis 29 and secured to the frame, which plate 39 has a notch 40 cut out therein to form a first coupling member.

The shape and the dimensions of the notch 40 are adapted to the shape and to the dimensions of a second coupling member such as a lug 41 provided, at the end of a control rod 42 (41 and 42 are shown. in FIGS. 1 to 5) forming part of the microprobe, such that these two complementary mechanical coupling members can provide a "temporary" mechanical connection between the control rod 42 and the vehicle 28.

With reference to FIGS. 1 to 5, the control rod 42 extends along the axis 27 and is mounted to be movable in translation and in rotation along and about this axis, inside a leaktight tubular sheath 43 extending likewise along this axis.

The sheath 43 is fastened to the airlock 26 at a first one of its two longitudinal ends, and it is closed at its second longitudinal end.

A motion transmission member 44 is slidably mounted relative to the axis 27 to slide around and along the sheath 43.

This transmission member 44 is connected by a magnetic connection to the control bar, or rod, 42 so that the movements of the member 44 in translation and in rotation along and about the axis 27 are transmitted to the control bar 42.

As described below with reference to FIGS. 3 to 5, the slidable control bar 42 serves to move the sample support vehicle 28 from the airlock to the motion object, and back again.

The analysis device also has a plurality of manipulator members 46 each comprising a bar 47 provided at a first one of its ends with a gripper for manipulator) tool 48 such as a clamp, and provided at its second end with a control tool 49, such as a handle, that is connected to the manipulator tool 48.

Each member 46, and in particular each bar 47, extends through. an orifice 130 to 132 pierced through the wall 13 of the cell 11 so as to enable an operator situated outside the cell 11 and acting on the control tool 49 to actuate the gripper tool 48 of the member 46 under consideration, which gripper tool is situated inside the cell 11.

In FIGS. 1 to 5, each gripper tool 48 is always represented by the tip of an arrow, while each control tool 49 is represented diagrammatically by a black lozenge.

Thus, the manipulator member 46 shown in FIG. 1 allows an operator acting on this member to cause the gripper tool of the member to engage a drive wheel 50 that is itself engaged with a respective one of the three wormscrews 24 used for driving movement of the table 22 via a mechanical transmission connection 62 diagrammatically represented. in the figure by an angled line.

This enables the operator to act manually on the control tool 49 to bring the sample support 20 that is present in the analysis chamber into alignment with means for transferring the sample to the airlock, in particular in the event of a failure of the power supply to the drive motors of the XYZ-table.

This makes it possible more particularly to align the guide rails of the airlock with the guide rails of the motion object, which rails are described below.

For each axis of the table 22, the analysis device has a position sensor (not shown) that senses the position of the table along that axis, and a display device (not shown) connected to the sensor in order to display the position of the table along that axis, the display being visible in a location outside the cell 11.

By way of example, for each movement axis of the table, this device for controlling the position of the table 22 may be constituted essentially by a mechanical revolution counter engaging the drive wheel 50, the transmission 62, and/or the screw 24.

With reference to FIGS. 2 to 5 in particular, the analysis device includes a system for transporting the sample support vehicle 28 from the glove box 15 to the airlock 26, and from the airlock to the support 20 carried by the motion object, and back again.

To transfer the vehicle 28 from the glove box 15 to the airlock 26, the device includes a transfer structure 63 mounted to be movable in translation relative to the airlock along an axis 51 that is substantially horizontal and that is at an angle relative to the axis 27, e.g. substantially perpendicular to the axis 27.

Figure 7:
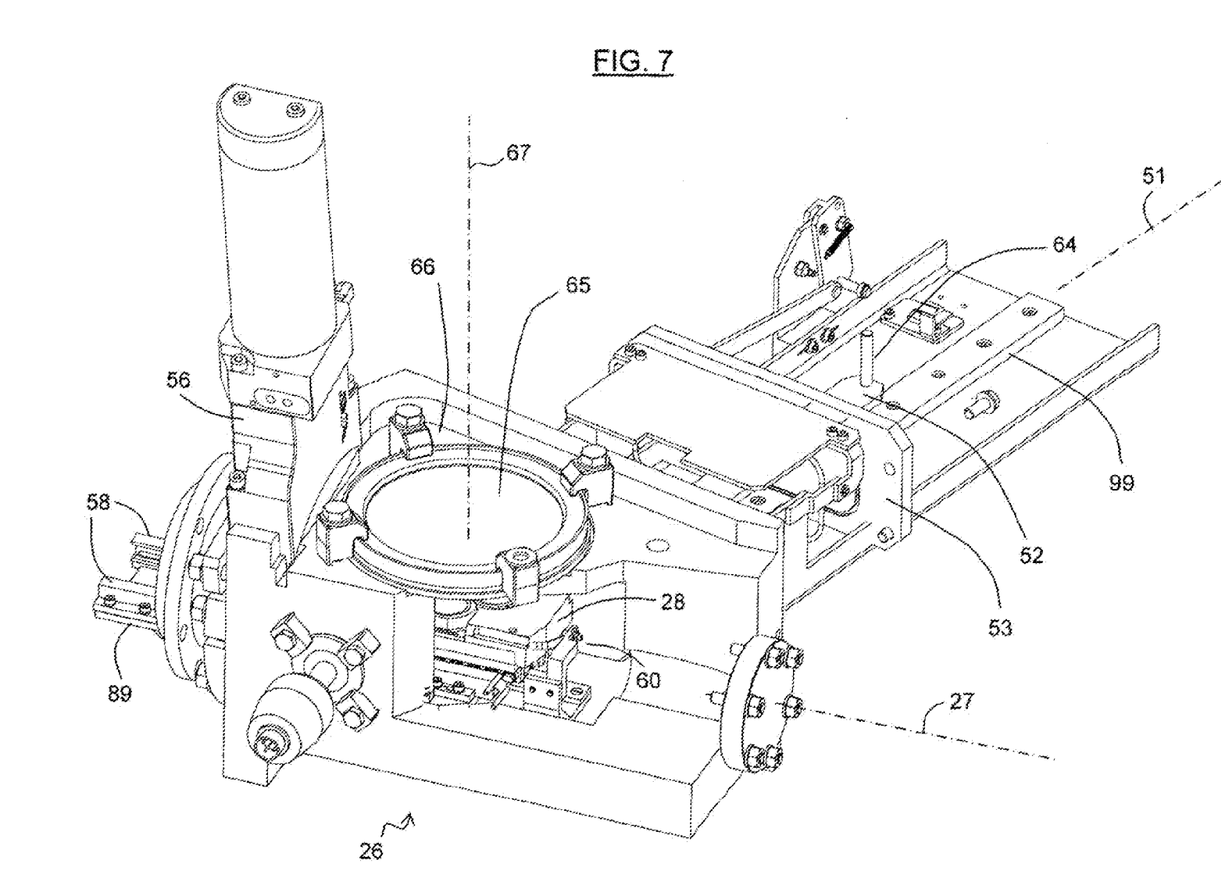
FIG. 7 is a partially cutaway perspective view of the airlock.

To this end, the transfer structure 63 may be slidably mounted on an elongate rail 99 extending along the axis 51 and secured to the structure defining the airlock 26, as shown in FIG. 7.

This transfer structure 63 has an elongate bar 52 extending along the axis 51 and two rail segments 35 and 36 parallel to the axis 27 that are secured to the bar 52 at a first end of the bar 52.

At its second. end, the bar 52 has a projection 64 enabling the bar to be moved along the axis 51 by means of a gripper tool 48 of a manipulator member 46 actuated by an operator.

The rail segments 35 and 36 may be identical to those shown in FIG. 6, facing each other and each capable of receiving one of the two rows of wheels of the vehicle 28 that they support.

The transfer structure 63 includes a plate 53 secured to the bar 52 and serving to close an opening 55 provided in a side wall 54 of the airlock in order to enable the airlock to be evacuated.

The microprobe includes a gate valve 56 serving to isolate the analysis chamber 18 from the airlock 26, and enabling a vacuum to be established in the chamber 18.

Each of: the airlocks 26; a stationary structure 89 extending inside the chamber 18 in line with the airlock (along the axis 27); and the support 20 carried, by the motion object, includes a respective pair of rails 57 to 59 for guiding the vehicle 28 while the vehicle is being moved along the axis 27 from the airlock to the support 20, and back again.

The rails 57 to 59 present identical spacing. The rails 57 and 58 are in alignment along two axes parallel to the axis 27. The rails 59 secured to the support 20 are also in alignment with the rails 57 and 58 in one position of the motion object, so as to enable the vehicle 28 to be transferred between the rails 58 and 59.

As mentioned above, when the drive motors of the motion object cannot be actuated in order to obtain this position of mutual alignment between the rails 58 and 59 so as to enable the vehicle to return into the airlock, it is possible to bring these rails into alignment by acting on the three drive wheels 50 of the three respective wormscrews 24.

In addition, each of the airlocks 26 and the support 20 includes a sensor 60 for detecting the presence of the vehicle 28.

The support 20 also includes a mechanical abutment 61 enabling the vehicle 28 to be held in the analysis position on the support 20.

Figure 2:
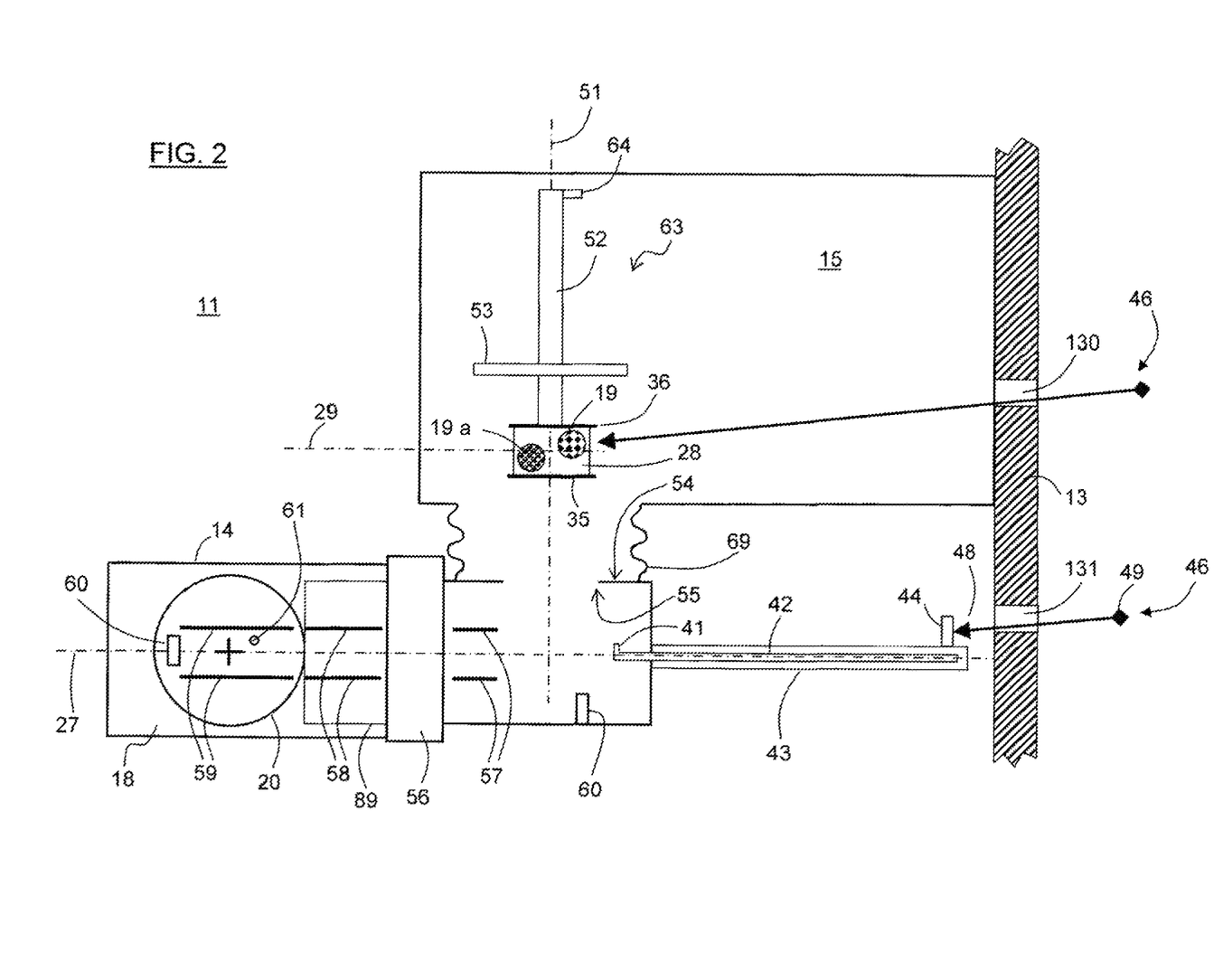
FIGS. 2 to 5 are diagrammatic plan views of the system for transferring a movable sample support from a secondary enclosure (a glove box in this example) to the motion object of the microprobe, and back again, in several distinct configurations.

With reference to FIGS. 2 to 5 in particular, the analysis device may be used as follows:

A sample 19 of material for analysis is placed in the glove box 15 (by means not shown).

An operator acting on the control handle 49 of a manipulator member 46 can place the sample 19 in a cup 90 of the vehicle 28 having its wheels engaged in the rails 35, 36 of the transfer structure 63, and having its longitudinal axis 29 parallel to the axis 27, as in the configuration shown in FIG. 2

Figure 3:
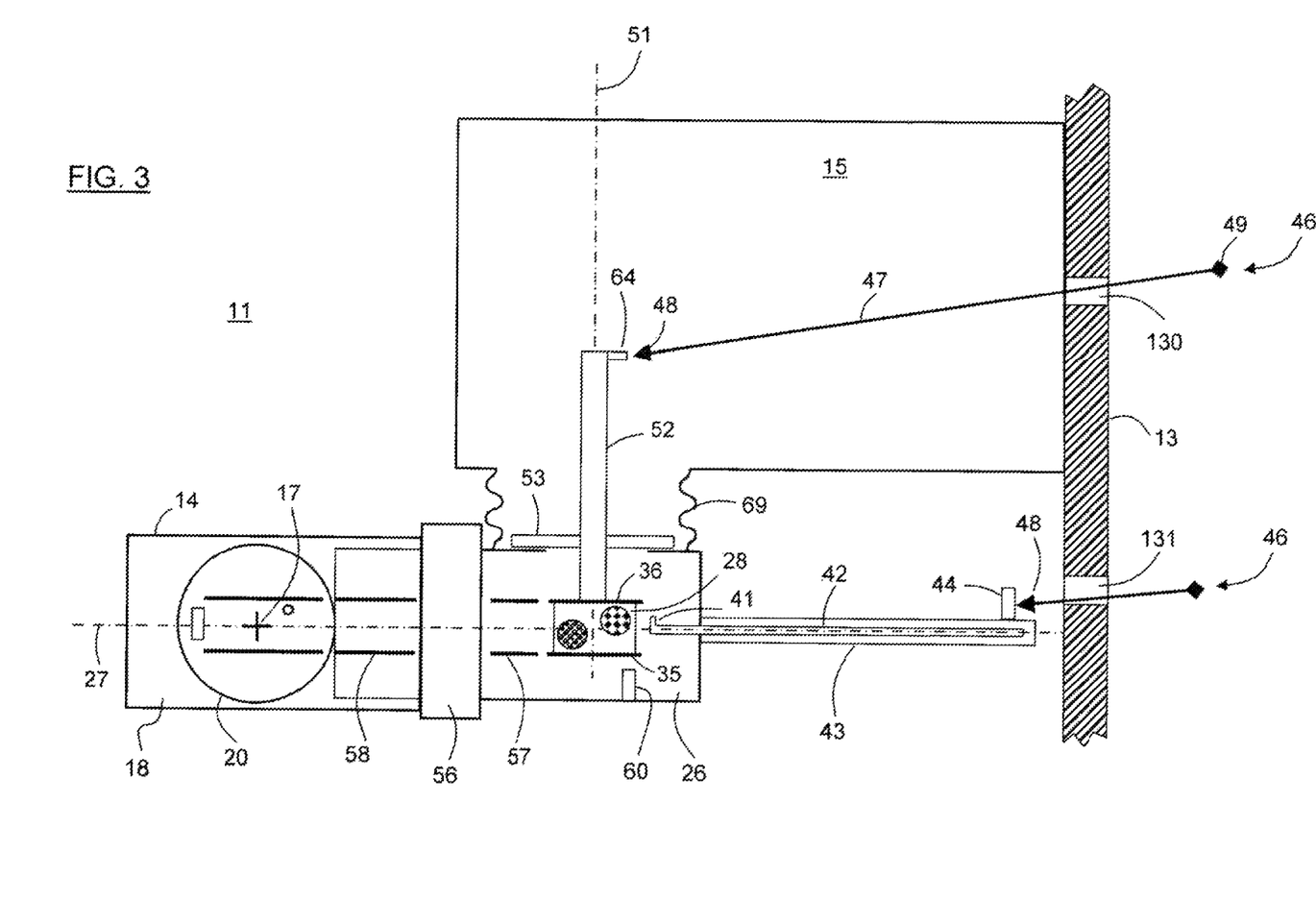

The operator can then engage the projection 64 of the gripper tool 48 of the member 46 and apply thrust to said projection so as to cause the structure 63 to slide along the axis 51 towards the airlock 26 until the plate 53 comes to press against the wall 54 of the airlock and until the rails 35, 36 come (simultaneously) into alignment with the rails 57 to 59, as in the configuration shown in FIG. 3.

In this configuration, since the valve 56 is closed and the through opening 55 provided in the wall 54 is shut by the plate 53, suction can be established inside the airlock 26 in order to reach a determined vacuum.

Once the desired vacuum has been reached, the coupling member 41 provided at the end of the control bar 42 is engaged in the notch 40 provided in the plate 39 of the vehicle 28, e.g. by moving the bar 42 in translation and in rotation as a result of an operator acting on the manipulator member 46 shown in FIG. 1, by means of the gripper tool 48 of that member acting on the motion transmission member 44.

Figure 4:
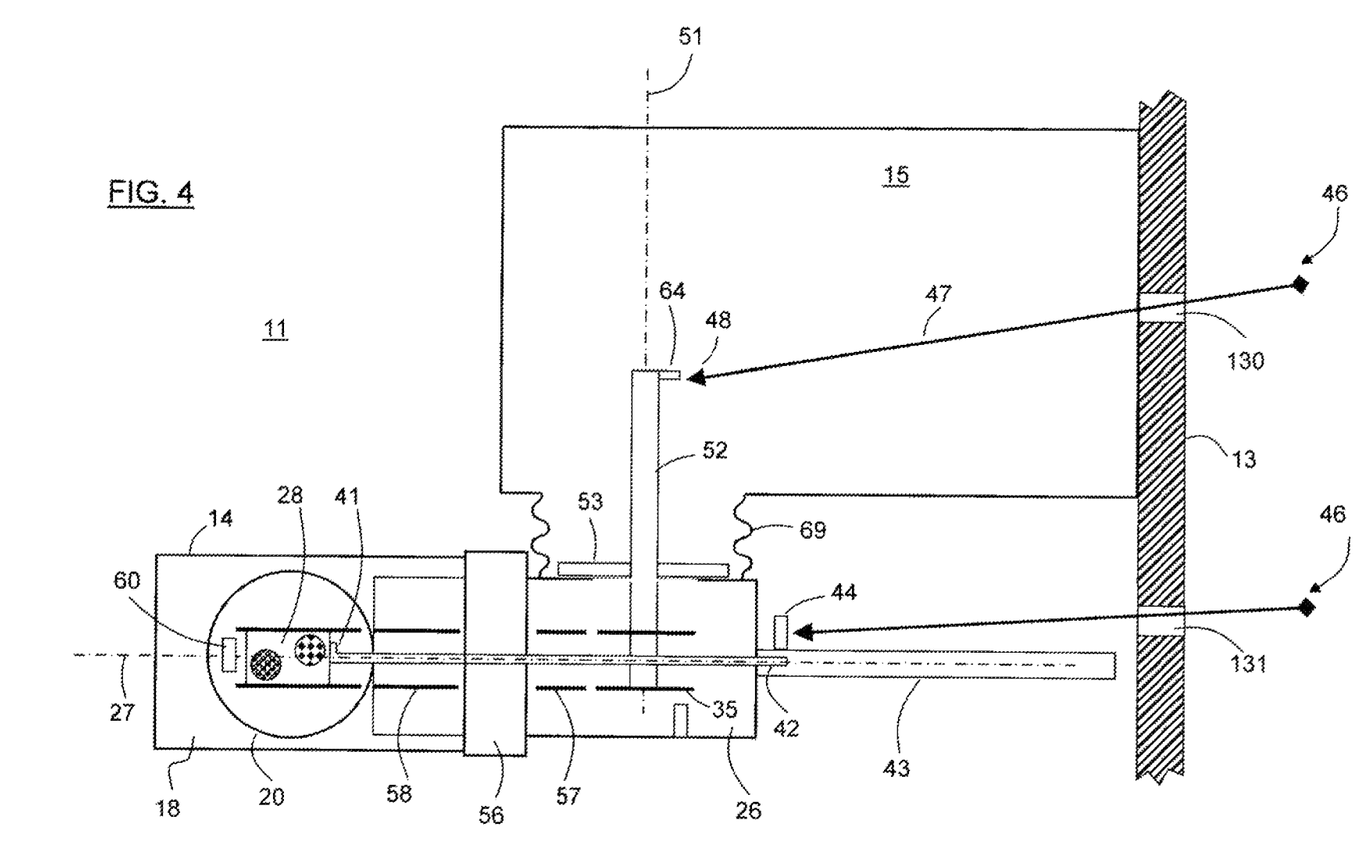

With the valve 56 being opened, the operator can then cause the vehicle 28 to run in succession on the rails 35 & 36, then 57, then 58, and then 59, until the vehicle 28 engages the abutment 61 on the support 20 carried by the motion object 22, with this corresponding to the configuration shown in FIG. 4, the operator doing this by acting on the same manipulator member 46 via the member 44 and the bar 42.

Figure 5:
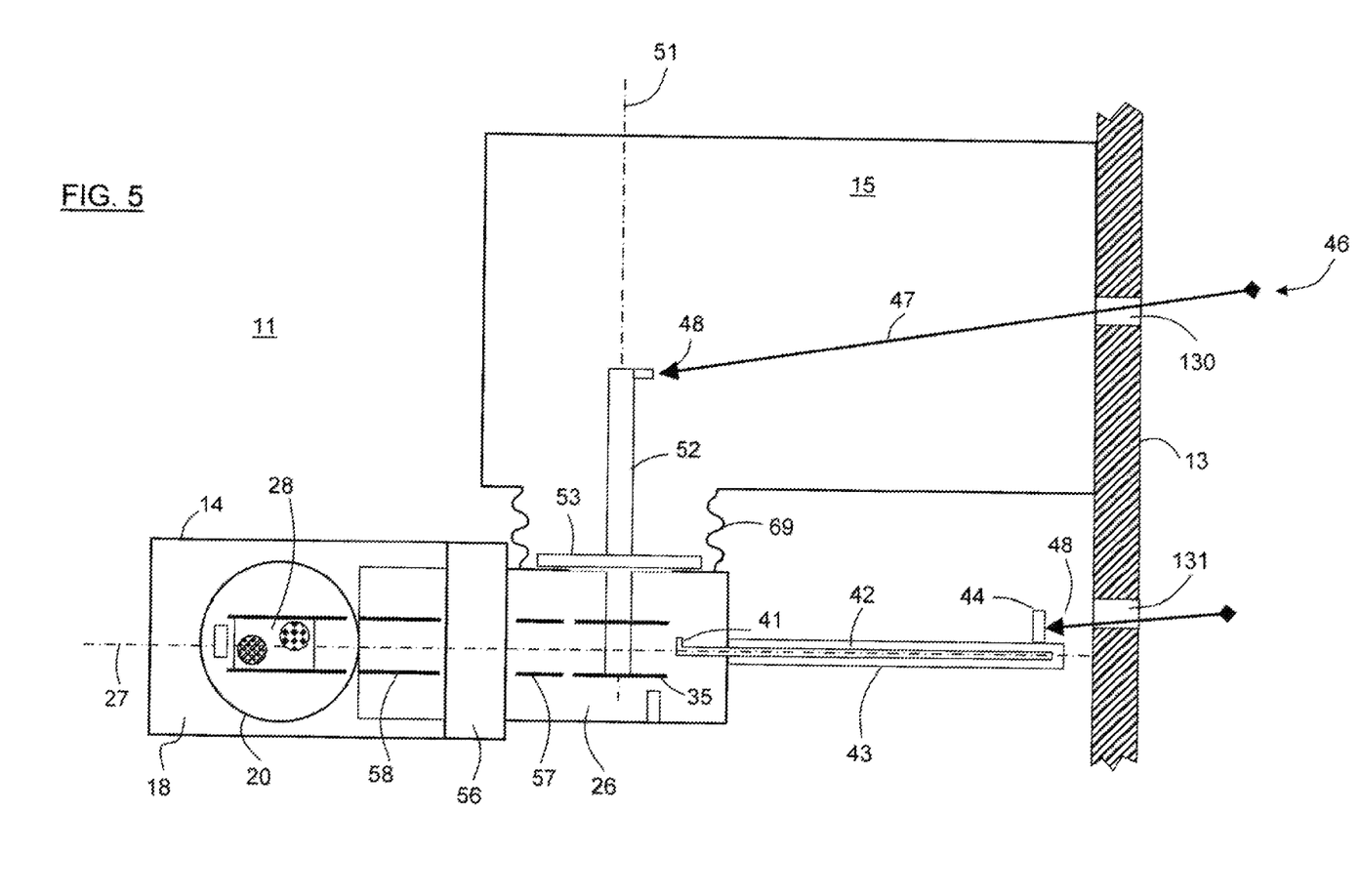

The coupling member 41 of the control bar 42 can then be disengaged from the coupling member 39, 40 of the vehicle 28, e.g. by moving the bar 42 in translation and in rotation as a result of the operator taking action on the member 44, and the bar 42 can be moved in the same manner to slide along the axis 27 so as to return into the sheath 43, as shown in FIG. 5.

Locking means that allow the vehicle 28 to be separated from the bar 42 in the analysis position of the vehicle 28 as shown in FIG. 4, and also in the transfer position of the vehicle 28 inside the airlock as shown in FIG. 3, while preventing such separation in all intermediate positions of the vehicle 28 between those two positions, may comprise a lug secured to the bar 42 and a track (provided inside the sheath) in which the lug engages, such that the bar 42 can pivot about the axis 27 in these two positions only.

With reference to FIGS. 1 and 7, in addition to the position of the sample carrier vehicle 28 being monitored by the sensors 60, visual inspection may be performed by having a transparent window 65 provided in the top wall 66 of the airlock, over the region of the airlock that receives the vehicle while being transferred between the glove box and the analysis chamber.

This visual inspection may be performed by means of a camera 68 placed inside the cell 11 and looking along a direction 67 at the window 65.

As shown in FIGS. 2 to 5, the analysis device includes a bellows 69 connecting the airlock to the glove box, the vehicle 28 being capable of moving inside the bellows so as to enable it to be transferred from the glove box to the airlock, and back again.

Such rustproof bellows make it possible to avoid the cell 11 being contaminated by the sample carried by the vehicle 28, and to limit, or eliminate the transmission of vibration from the glove box to the walls of the airlock and to the microprobe.

The invention claimed is:

1. A device for analyzing a sample of a material with the help of a microprobe, the device comprising:
    a main enclosure containing a secondary enclosure;
    a microprobe placed in the main enclosure and fitted with a motion object, the microprobe comprising:
        an analysis chamber for receiving the sample
        a gun for bombarding the sample placed in the analysis chamber, with a beam, along an axis of the gun,
        a column for focusing the beam on the sample, and
        Spectrometers arranged to receive X-rays emitted by the sample during interaction between the beam and the material of the sample;
        the motion object comprising an XYZ-table serving to move a sample zone that is subjected to bombardment along two orthogonal axes of a plane perpendicular to the axis of the gun and also along that axis;
    an airlock (26) placed in the main enclosure and connected to the microprobe and to the secondary enclosure; and
    a movable sample support for supporting the sample, the sample support being movable from the secondary enclosure to the airlock and from the airlock to the motion object;
    each of the airlock and the motion object including a respective member for guiding the movable sample support to guide the support while it is being moved, and also a respective sensor for detecting the presence of the movable sample support.

2. A device according to claim 1, wherein the motion object includes an abutment serving to hold the movable sample support in an analysis position.

3. A device according to claim 1, including a slidable control bar for moving the movable sample support from the airlock to the motion object and back again.

4. A device according to claim 3, wherein the movable sample support and the sliding control bar have respective complementary coupling members designed for engaging mutually so as to provide a mechanical connection between the control bar and the movable sample support.

5. A device according to claim 4, including locking means that enable the coupling members to be mutually separated in a position of the movable sample support on the motion object, referred to as the analysis position, and also in a position of the movable sample support inside the airlock, referred to as the transfer position, while preventing such separation in all other positions of the movable sample support that are intermediate between the analysis position and the transfer position.

6. A device according to claim 1, including alignment means for aligning the guide member of the airlock and the guide member of the motion object in the event of a power supply failure to the drive motors of the motion object.

7. A device according to claim 6, wherein, for each movement axis of the motion object, the alignment means comprise a drive member engaged with a wormscrew for driving the motion object along that axis, the drive member being actuatable by means of a manipulator member passing through the wall $_{(13)}$ of the main enclosure.

8. A device according to claim 6, wherein, for each axis of the motion object, the alignment means comprise a position sensor sensitive to the position of the motion object along that axis, and a display device connected to the sensor to display the position of the motion object along that axis in a manner that is visible from outside the main enclosure.

9. A device according to claim 1, wherein at least one of the guide members comprises a rail segment on or against which the movable sample support can slip, slide, or roll.

10. A device according to claim 1, wherein the movable sample support is fitted with skids and/or wheels to facilitate its movement on or along the guide member.

11. A device according to claim 1, wherein a wall of the airlock is transparent.

12. A device according to claim 1, wherein the movable sample support includes a visible mark.

13. A device according to claim 1, including a hollow structure connecting the airlock to the secondary enclosure, within which the movable sample support can move so as to enable the movable sample support to be transferred from the secondary enclosure to the airlock, and back again.

14. A device according to claim 13, wherein the hollow structure comprises a dustproof covering presenting low mechanical stiffness so as to limit any transmission of vibration from the secondary enclosure to the airlock, the hollow structure possibly being essentially constituted by a corrugated tubular covering made of a plastics material, in particular a covering in the form of a bellows.

15. A device according to claim 1, wherein the main enclosure is defined by shielded walls.

16. A device according to claim 1, wherein the secondary enclosure is a glove box maintained at a pressure that is lower than the pressure inside the main enclosure.

\* \* \* \* \*